US012178569B2

(12) United States Patent
Jain et al.

(10) Patent No.: US 12,178,569 B2
(45) Date of Patent: *Dec. 31, 2024

(54) SYSTEMS AND METHODS FOR OBJECT SIZE ESTIMATION

(71) Applicant: Boston Scientific Medical Device Limited, Galway (IE)

(72) Inventors: Ashish Jain, Uttar Pradesh (IN); Denise C. Lane, Bedford, NH (US)

(73) Assignee: Boston Scientific Medical Device Limited, Galway (IE)

( * ) Notice: Subject to any disclaimer, the term of this patent is extended or adjusted under 35 U.S.C. 154(b) by 54 days.

This patent is subject to a terminal disclaimer.

(21) Appl. No.: 18/047,752

(22) Filed: Oct. 19, 2022

(65) Prior Publication Data
US 2023/0065176 A1  Mar. 2, 2023

Related U.S. Application Data

(63) Continuation of application No. 16/397,243, filed on Apr. 29, 2019, now Pat. No. 11,504,026.
(Continued)

(51) Int. Cl.
*A61B 5/107*   (2006.01)
*A61B 90/92*   (2016.01)

(52) U.S. Cl.
CPC ............ *A61B 5/1076* (2013.01); *A61B 90/92* (2016.02)

(58) Field of Classification Search
CPC .................................................... A61B 5/1076
See application file for complete search history.

(56) References Cited

U.S. PATENT DOCUMENTS 6,402,771 B1    6/2002  Palmer et al.
6,613,002 B1 *  9/2003  Clark ................... A61B 5/1076
                                              600/587
(Continued)

FOREIGN PATENT DOCUMENTS

DE    19953359 A1    5/2000
EP     0941036 A1    9/1999
(Continued)

OTHER PUBLICATIONS

Cordes, J. et al., "A comparison between an in vitro ureteroscopic stone size estimation and the stone size measurement with the help of a scale on stone baskets," World J. Urol. (2016), vol. 34, pp. 1303-1309.
(Continued)

*Primary Examiner* — Alexander J Orkin
(74) *Attorney, Agent, or Firm* — Bookoff McAndrews, PLLC

(57) ABSTRACT

A medical device may include a handle assembly having an actuator and a sheath. The sheath may extend between a proximal end and a distal end. The proximal end of the sheath may be coupled with the actuator. The medical device may further include an end-effector moveable relative to the sheath between an extended configuration and a retracted configuration. The end-effector may include a plurality of expandable legs. Each of the plurality of expandable legs may include a plurality of first indicia and a plurality of second indicia. A color of each of the first plurality of indicia may be different than a color of each of the second plurality of indicia.

15 Claims, 2 Drawing Sheets

Related U.S. Application Data

(60) Provisional application No. 62/664,793, filed on Apr. 30, 2018.

(56) References Cited

U.S. PATENT DOCUMENTS

| | | | |
|---|---|---|---|
| 11,504,026 B2* | 11/2022 | Jain | A61B 17/221 |
| 2001/0031971 A1 | 10/2001 | Dretler et al. | |
| 2002/0042582 A1 | 4/2002 | Vrba et al. | |
| 2002/0111567 A1 | 8/2002 | Vanden Hoek et al. | |
| 2003/0135223 A1 | 7/2003 | Teague et al. | |
| 2004/0133129 A1* | 7/2004 | Harari | A61B 5/1076 |
| | | | 600/585 |
| 2004/0138692 A1 | 7/2004 | Phung et al. | |
| 2004/0199200 A1* | 10/2004 | Teague | A61B 17/221 |
| | | | 606/113 |
| 2005/0010138 A1* | 1/2005 | Mangiardi | A61B 5/1076 |
| | | | 600/587 |
| 2005/0143770 A1 | 6/2005 | Carter et al. | |
| 2006/0064039 A1 | 3/2006 | Griego et al. | |
| 2007/0239141 A1 | 10/2007 | Hartley et al. | |
| 2009/0082780 A1 | 3/2009 | Lu et al. | |
| 2009/0162531 A1 | 6/2009 | Nesbitt | |
| 2011/0196410 A1 | 8/2011 | Besselink et al. | |
| 2013/0184741 A1 | 7/2013 | Laroya et al. | |
| 2014/0058251 A1* | 2/2014 | Stigall | A61B 6/12 |
| | | | 600/407 |
| 2016/0199079 A1 | 7/2016 | Chu et al. | |
| 2016/0235498 A1 | 8/2016 | Stanley et al. | |
| 2016/0256179 A1 | 9/2016 | Walish et al. | |
| 2017/0007279 A1 | 1/2017 | Sharma | |
| 2017/0325829 A1 | 11/2017 | Chae | |
| 2018/0028218 A1 | 2/2018 | Pereira et al. | |

FOREIGN PATENT DOCUMENTS

| | | |
|---|---|---|
| WO | WO 99/16365 A1 | 4/1999 |
| WO | WO 9916363 A1 | 4/1999 |
| WO | 2016148381 A1 | 9/2016 |

OTHER PUBLICATIONS

Cordes, J. et al., "A comparison between an in vitro ureteroscopic stone size estimation and the stone size measurement with the help of a scale on stone baskets," World Journal of Urology, Sep. 2016, vol. 34, Issue 9, https://link.springer.com/article/10.1007%2Fs00345-016-1774-x, last accessed Feb. 16, 2018, 6 pages.

Cordes, J. et al., "Measurement of Stone Diameter with Three Sizes of Automatically Fixating Stone Baskets," Open Journal of Urology, vol. 3, No. 2, 2013, http://file.scirp.org/Html/3-5000138_31320.html, last accessed Feb. 16, 2018, 8 pages.

Communication Relating to the Results of the Partial International Search from corresponding international application PCT/IB2019/053495, dated Sep. 6, 2019.

Chinese Office Action in Application No. 201980028935.1, dated Aug. 29, 2024 (5 pages).

* cited by examiner

SYSTEMS AND METHODS FOR OBJECT SIZE ESTIMATION

CROSS-REFERENCE TO RELATED APPLICATIONS

This patent application is a continuation of U.S. patent application Ser. No. 16/397,243, filed Apr. 29, 2019, which claims the benefit of priority under 35 U.S.C. § 119 to U.S. Provisional Patent Application No. 62/664,793, filed Apr. 30, 2018, each of which is herein incorporated by reference in its entirety.

TECHNICAL FIELD

The present disclosure relates generally to medical systems, devices, and related methods. More specifically, the present disclosure relates to medical systems and/or devices for treating tissue and/or removing objects within the body of a patient.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, and gallbladder. Minimally invasive medical procedures are used to remove these concretions through natural orifices, or through an incision, such as during a percutaneous nephrolithotomy (PNCL) procedure.

In order to remove such concretions (e.g., kidney stones), a medical device, such as a retrieval device (e.g., an expandable basket), may be delivered through a working channel of an insertion device. The shaft of such a medical device may be selectively extended and retracted relative to the working channel of the insertion device or a sheath of the medical device to deploy or retract an end-effector (e.g., basket) to perform one or more therapies, treatments, or diagnostic evaluations on a subject. For example, the end-effector may be deployed to capture a stone or other such material therein for removal through the working channel. If, however, the stone is so large that it cannot pass through the working channel, a medical professional may be required to either manipulate the medical device so as to remove the stone from the end-effector if possible, or one or more additional procedures may be required to fragment the stone (e.g., lithotripsy or the like) so as to enable passage through the working channel. Often, however, the only way gauge the size of the stone is through a process of trial-and-error in which a captured stone is withdrawn toward the working channel of an insertion device to see if the stone can physically pass therethrough. Such trial-and-error processes increase procedure time and may result in damage to surrounding patient tissue, the end-effector, and/or the insertion device itself.

The systems, devices, and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

In one example, a medical device may include a handle assembly having an actuator and a sheath. The sheath may extend between a proximal end and a distal end. The proximal end of the sheath may be coupled with the actuator. The medical device may further include an end-effector moveable relative to the sheath between an extended configuration and a retracted configuration. The end-effector may include a plurality of expandable legs. Each of the plurality of expandable legs may include a plurality of first indicia and a plurality of second indicia. A color of each of the first plurality of indicia may be different than a color of each of the second plurality of indicia.

Examples of the medical device may include one or more of the following features. The color of each of the second plurality of indicia may be darker than the color of each of the first plurality of indicia. The color of each of the first indicia may be white or the color of each of the first indicia may be blue. The color of each of the second indicia may be black. The first plurality of indicia and the second plurality of indicia may alternate along a length of each leg of the plurality of legs. Each of the first plurality of indicia may include a first coefficient of friction and each of the second plurality of indicia may include a second coefficient of friction greater than the first coefficient of friction. Each of the first plurality of indicia may include a physical attribute and each of the second plurality of indicia may be free from said physical attribute. The physical attribute of each of the first plurality of indicia may include one or more of a protrusion, a bump, an extension, a tine, a groove, a cutout, a depression, or a recess. A length of each of the first indicia may be the same. A length of each of the second indicia may be the same. The length of each of the first plurality of indicia may be the same as the length of each of the second plurality of indicia. The length of each of the first plurality of indicia and the second plurality of indicia may be between about 0.5 mm and about 3.0 mm. The length of each of the first plurality of indicia and the second plurality of indicia may be 2.0 mm. The length of each of the first plurality of indicia may be different than the length of each of the second plurality of indicia. The plurality of legs may include between 3 and 8 legs.

In a further example, a method may include inserting a medical device into a location within a subject's body. Additionally, the method may include moving an end-effector of the medical device to an extended and expanded configuration, wherein the end-effector may include a plurality of legs. Further, the method may include capturing an object with the plurality of legs of the end-effector and measuring a size of the object via a plurality of first indicia and a plurality of second indicia alternatingly disposed along at least one of the plurality of legs. A color of each of the first plurality of indicia may be different than a color of each of the second plurality of indicia.

Examples of the method may include one or more of the following features. Measuring the size of the object may include measuring a first dimension of the object and the method may further include measuring a second dimension of the object. The second dimension may be generally orthogonal to the first dimension. The method may include manipulating an orientation of the object relative to the end-effector. The manipulating may include applying a distally directed force on a guidewire to impact or contact the object.

In a further example, a medical device may include a handle assembly including an actuator. The medical device also may include a sheath extending between a proximal end and a distal end. The proximal end of the sheath may be coupled with the actuator. The medical device may further include an end-effector moveable relative to the sheath between an extended configuration and a retracted configuration. The end-effector may include a plurality of expandable legs. At least one of the plurality of expandable legs may include a plurality of first indicia. A length of each of the first indicia may be the same. At least one of the plurality of expandable legs may include a plurality of second indicia. A length of each of the second indicia may the same. The length of each of the first plurality of indicia may be the same as the length of each of the second plurality of indicia. The first plurality of indicia and the second plurality of indicia may alternate along a length of each leg of the plurality of legs. A color of each of the first plurality of indicia may be different than a color of each of the second plurality of indicia.

Examples of the medical device may further include one or more of the following features. Each of the plurality of legs may include the first plurality of indicia and the second plurality of indicia. The color of each of the second plurality of indicia may be darker than the color of each of the first plurality of indicia. The length of each of the first plurality of indicia and the second plurality of indicia may be between about 0.5 mm and about 3.0 mm. The length of each of the first plurality of indicia and the second plurality of indicia may be 2.0 mm. The color of each the first plurality of indicia may be white or the color of each of the plurality of first indicia may be blue, and the color of each of the second indicia may be black.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical devices for treating internal areas of a patient's body. The medical device may include an end-effector including a plurality of indicia.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the patient or closer to a medical professional using the medical device or insertion device. In contrast, "distal" refers to a position relatively further away from the medical professional using the medical device or insertion device, or closer to the interior of the patient.

Figure 1:
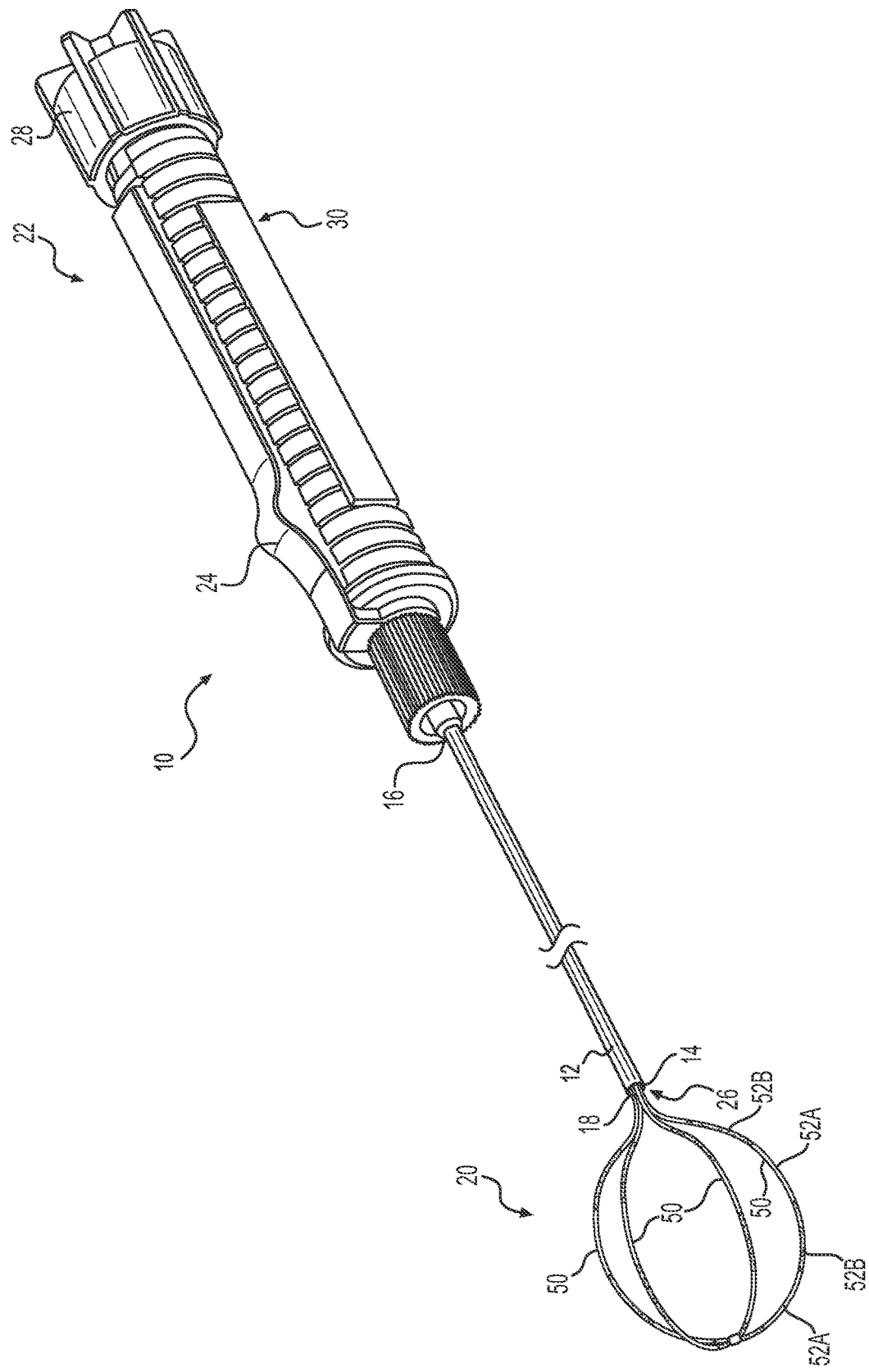
FIG. 1 illustrates an exemplary medical device in an extended and expanded configuration.

FIG. 1 illustrates an exemplary medical device 10. Medical device 10 includes a sheath 12 including a distal end 14 and a proximal end 16. Sheath 12 may be, for example, a hollow tube and include a longitudinally-extending lumen 26. Sheath 12 may be made of a polymer material, metal, or a combination of materials. Medical device 10 may also include a shaft 18 coupled to (e.g., via any appropriate connection mechanism such as, for example, laser welding, adhesives, and/or mechanical fasteners, etc.) or integrally (e.g., monolithically) formed with an end-effector 20 at the distal end thereof. Shaft 18 may be elongated, and may include, for example, a wire, braid, shaft, and/or any other suitable drive member configured to transfer translational and/or rotational forces from its proximal end to its distal end.

Figure 2A:
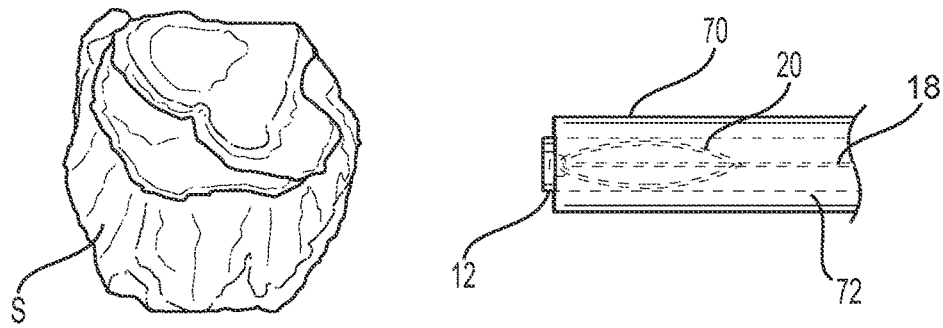
FIG. 2A illustrates the medical device of FIG. 1 in a retracted and collapsed configuration within a working channel of an insertion device.
Figure 2B:
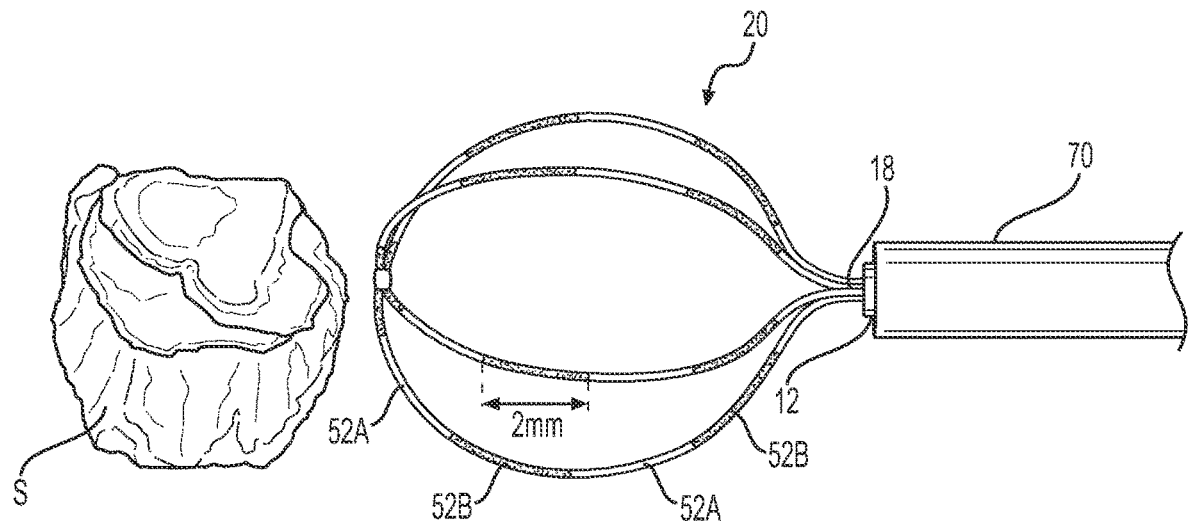
FIG. 2B illustrates the medical device of FIG. 1 in an extended and expanded configuration adjacent an object of interest.
Figure 2C:
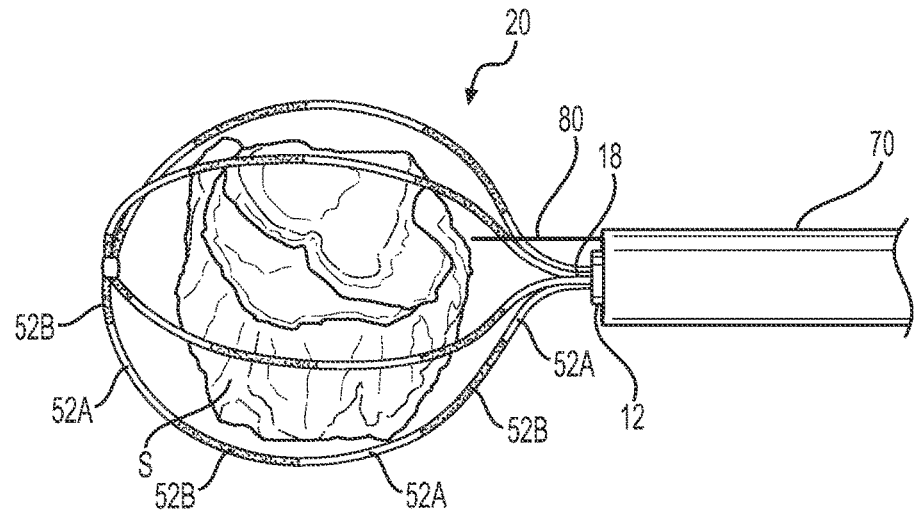
FIG. 2C illustrates the medical device of FIG. 1 in an extended and expanded configuration after capturing an object of interest therein.

As shown, end-effector 20 may comprise a cage or basket configured to capture and/or retrieve material (e.g., a stone S, FIGS. 2A-2C). End-effector 20 may be laser cut from a tube and/or chemically etched, and be comprised of any appropriate material, such as, for example, shape memory materials including synthetic plastics, stainless steel, and superelastic metallic alloys of nickel/titanium (e.g., Nitinol), copper, cobalt, vanadium, chromium, iron, or the like; or alternative materials including, for example, other metal alloys, powdered metals, ceramics, thermal plastic composites, ceramic composites, and polymers. Also, combinations of these and other materials can be used.

End-effector 20 and shaft 18 may be movable relative to sheath 12 between an extended and expanded state (FIG. 1) and a retracted and collapsed state (FIG. 2A). For example, medical device 10 may include a handle assembly 22 at the proximal end 16 of sheath 12. Handle assembly 22 may include an actuation member 24 for moving sheath 12 relative to end-effector 20 so as to transition end-effector 20 between the extended state and the retracted state. For example, proximal end 16 of sheath 12 may be secured to actuator 24 while a proximal end of shaft 18 may be secured to handle assembly 22 via a lock 28 in any appropriate manner (e.g., via a vise, friction, adhesives, welding, and/or heat staking, etc.). Lock 28 may be threadably coupled a proximal end of handle assembly 22. When so coupled, lock 28 maintains an axial position of shaft 18 relative to a grip 30 of handle assembly 22. That is, lock 28 prevents axial translation of shaft 18 relative to grip 30 of handle assembly 22.

In use, a medical professional may urge actuator 24 distally relative to a grip 30 so as to move end-effector 20 between the extended state (FIG. 1) and the retracted state (FIG. 2A). For example, a medical professional may hold grip 30 within the palm of their hand with their thumb or finger on actuator 24. In order to move end-effector 20 from the extended state to the retracted state, the medical professional may push, slide, or advance actuator 24 relative to grip 30. Due to the connection of sheath 12 to actuator 24, moving actuator 24 distally results in distal movement of sheath 12 towards or over end-effector 20. Upon advancement of sheath 12 over end-effector 20, end-effector 20 transitions (e.g., collapses, compresses, etc.) to its retracted state within lumen 26 of sheath 12.

End-effector 20, as described above, may be a basket or retrieval device including a plurality of legs 50. For example, as shown in FIG. 1, end-effector 20 may include four legs 50. In other arrangements, however, end-effector 20 may include more or fewer than four legs 50. For example, end-effector 20 may include between about 3 and about 8 legs. Each such leg 50 may include a plurality of graduations, markings, or indicia thereon. For example, each leg 50 may include a plurality of first indicia 52A and a plurality of second indicia 52B. First indicia 52A and second indicia 52B may be alternatingly disposed along a length of each leg 50. For example, each leg may include a pattern of indicia beginning with first indicia 52A followed by second indicia 52B, and repeat thereafter along the length of each leg 50. Each of first indicia 52A may have a first color, while each of second indicia 52B may have a second color. The second color of the second indicia 52B may be generally darker in the visual spectrum of light (e.g., may have a higher wavelength) than the first color of the first indicia 52A. For example, the second indicia 52B may be black while the first indicia 52A may be white or blue. While these colors enable a sufficient contrast so as to be readily differentiated by a medical professional, it is understood that specific references to colors are merely descriptive and the disclosure is not so limited. Rather, the second color of the second indicia 52B may be any color that is sufficiently different than the first indicia 52A so as to enable visual differentiation between the first indicia 52A and the second indicia 52B by a medical professional during use. Optionally, either first indicia 52A or second indicia 52B may include a colored coating, while the other of first indicia 52A or second indicia 52B may be uncoated so as to have a different color (e.g., a color of a bare wire or the like).

In some arrangements, each first indicia 52A and second indicia 52B include a common length, e.g., 2 mm. While a length of 2 mm is described herein and depicted (e.g., FIG. 2B), the disclosure is not so limited. Rather, the length of an indicia, e.g., first indicia 52A and/or second indicia 52B may be any appropriate length (e.g., 0.5 mm, 1 mm, 1.5 mm, 2.5 mm, 3 mm, or fractions therebetween, etc.) to facilitate estimation of a stone S size by a medical professional, as will be described in further detail below. Alternatively, each of the first indicia 52A may have a first length (e.g., 2 mm) while each of the second indicia 52B may have second length (e.g., 1 mm). In either arrangement, a length of each of first indicia 52A second indicia 52B, whether common or differing, may be provided to the medical professional to facilitate estimation of stone S size by a medical professional, as will be described in further detail below In some arrangements, first indicia 52A may include a frictional coefficient different than second indicia 52B. For example, a coefficient of friction of first indicia 52A may be greater than a coefficient of friction of second indicia 52B, or vice versa. Such differing coefficients of friction may enable the different indicia lengths to alternately grip and slide on the uneven surface of a stone so as to manipulate and capture it in an optimal orientation for removal. Further, first indicia 52A may optionally include one or more additional physical attributes different than second indicia 52B, or vice versa. For example, first indicia 52A may include one or more protrusions, bumps, extensions, or tines extending radially outward of leg 50 relative to a longitudinal axis of leg 50 while second indicia 52B may not include or be free from such physical attributes, or vice versa. Alternatively, first indicia 52A may include one or more grooves, cutouts, depressions, recesses, or the like extending radially inward toward leg 50 relative to the longitudinal axis of leg 50 while second indicia 52B may not include or be free from such physical attributes, or vice versa. In either manner, a varied gripping profile along each leg 50 of end-effector 20 may be achieved.

In some arrangements, end-effector 20 may be formed from a tube. For example, a method of end-effector 20 formation may involve starting with a hollow tube or cannula. In such a case, shaft 18 may include such a hollow tube or cannula. At least a portion of the hollow tube or cannula may then be cut (e.g., laser cut), Accordingly, end-effector 20 may be monolithically formed from a single piece of material. Alternatively, end-effector 20 may be formed from multiple separate and distinct legs 50 coupled to one another in any appropriate fashion.

Medical device 10 may be delivered into a subject's body via any appropriate insertion device 70 having a working channel 72 extending therethrough. Insertion device 70 may include any device configured to allow a user to access and view internal areas of a subject's body such as, for example, a ureteroscope, a hysteroscope, a uteroscope, a bronchoscope, a cystoscope, and similar devices.

In use, a medical professional may position insertion device 70 at a desired location within the subject's body (e.g., at a location within the urinary tract of the subject). Such a location may be proximate a stone S or other such material to be captured by end-effector 20. Next, the medical professional may deliver medical device 10 in the subject's body via working channel 72 of insertion device 70. For example, distal end 14 of sheath 12 may be advanced through working channel 72 as shown in FIG. 2A.

Next, end-effector 20 may be moved to the expanded and extended configuration, as shown in FIG. 2B, via manipulation of one or both of actuator 24 and grip 30 relative to the other of actuator 24 and grip 30, as described above. Once so arranged, end-effector 20 may be manipulated to capture stone S therein, as shown in FIG. 2C. Once received therein, the medical professional may estimate the size of stone S via first indicia 52A and second indicia 52B. For example, while viewing internal areas of the subject's body via any appropriate imaging modalities (e.g., via a camera associated with insertion device 70) the medical professional may readily count how many first indicia 52A and second indicia 52B are required to extend along a first dimension of stone S (e.g., a dimension generally coaxial or parallel with a longitudinal axis of sheath 12), thereby gauging a size of stone S along the first dimension. For example, as shown in FIG. 2C, in which each of first indicia 52A and second indicia 52B have a common length of 2 mm, stone S has a dimension in a first direction extending along about 3 indicia (e.g., one first indicia 52A and two second indicia 52B) suggesting a total dimension of 6 mm (e.g., 3×2 mm=6 mm).

Next, the medical professional may visually inspect a general shape of stone S to determine whether a second dimension of stone S generally orthogonal to the first dimension is approximately the same. For example, if stone S is generally spherical, as shown in FIG. 2A-2C, the medical professional may determine that a second dimension of stone S that is generally orthogonal to the first dimension (e.g., generally orthogonal to a longitudinal axis of sheath 12) is also approximately 6 mm. If however, the stone S is oblong and/or not generally spherical in shape, the medical professional may estimate the second dimension of stone S based on the estimation of the first dimension of the stone S. For example, if the first dimension of stone S appears approximately double to the second dimension of stone S, then the medical professional may determine that the second dimension of stone S is about 3 mm (e.g., 6 mm/2=3 mm). Optionally, however, a medical professional may manipulate stone S relative to end-effector 20 so as to rotate or adjust an orientation of stone S within end-effector 20 and then directly visualize the dimension of stone S along the longitudinal axis of sheath 12. For example, the medical professional may manipulate actuator 24 and grip 30 to adjust the orientation of stone S. Optionally, one or more additional medical devices such as a guidewire 80 (FIG. 2C) or the like may be delivered through working channel 72 of insertion device 70 or through sheath 12 to push, prod, or adjust stone S relative to end-effector 20. For example, a medical professional may apply a distally-directed force on guidewire 80 so as to contact or impact stone S so as to manipulate an orientation of stone S.

Upon estimating the size of stone S, a medical professional may quickly and effectively determine whether one or more procedures are necessary to fragment or otherwise reduce the size of stone S prior to removal. For example, if the stone is estimated to have a size larger than a known dimension (e.g., diameter) of working channel 72, the medical professional need not withdraw the stone S toward insertion device 70 only to find by trial-and-error that it is too large to pass through working channel 72, thereby avoiding potential damage to end-effector 20 or insertion device 70. That is, indicia 52A and 52B provide a readily available in vivo size estimation of a stone S to be captured via an end-effector 20. As such, procedure time and cost may be reduced as there is a reduction in trial-and-error removal of a stone S having a size too large to pass through working channel 72 of insertion device 70.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device, comprising:
   a handle assembly including an actuator;
   a sheath extending between a proximal end and a distal end, the proximal end of the sheath being coupled with the actuator; and
   an end-effector moveable relative to the sheath between an extended configuration and a retracted configuration, the end-effector including a plurality of expandable legs, each of the plurality of expandable legs including a plurality of first indicia and a plurality of second indicia;
   wherein each of the first plurality of indicia has a first color;
   wherein each of the second plurality of indicia has a second color different from the first color;
   wherein (i) each of the first plurality of indicia, (ii) each of the second plurality of indicia, or (iii) each of the first plurality of indicia and each of the second plurality of indicia includes a physical attribute extending radially outwards or inwards relative to a longitudinal axis of the respective leg, and
   wherein a length of each of the first plurality of indicia and a length of each of the second plurality of indicia are substantially the same, and the length of each of the first plurality of indicia and the length of each of the second plurality of indicia is between about 0.5 mm and about 3.0 mm.

2. The medical device of claim 1, wherein the first plurality of indicia and the second plurality of indicia alternate along a length of each leg of the plurality of legs.

3. The medical device of claim 1, wherein the second color of each of the second plurality of indicia is darker than the first color of each of the first plurality of indicia.

4. The medical device of claim 1, wherein the physical attribute includes one or more of a protrusion, bump, extension, tine, groove, cutout, depression, or recess.

5. The medical device of claim 4, wherein each of the first plurality of indicia and each of the second plurality of indicia includes the physical attribute.

6. The medical device of claim 5, wherein the physical attribute of each of the first plurality of indicia is different from the physical attribute of each of the second plurality of indicia.

7. The medical device of claim 1, wherein the length of each of the first plurality of indicia and the length of each of the second plurality of indicia is about 2.0 mm.

8. The medical device of claim 1, wherein each of the first plurality of indicia include a first coefficient of friction and each of the second plurality of indicia include a second coefficient of friction, and the second coefficient of friction is different from the first coefficient of friction.

9. The medical device of claim 1, wherein the end-effector is monolithic.

10. A medical device, comprising:
    a handle assembly;
    a sheath, a proximal end of the sheath being coupled with the handle assembly;
    an end-effector moveable relative to the sheath between an extended configuration and a retracted configuration; the end-effector including at least one expandable leg, the at least one expandable leg including:
        a plurality of first indicia, wherein each of the plurality of first indicia includes a coating having a first color, wherein a length of each of the first indicia is the same; and
        a plurality of second indicia, wherein each of the plurality of second indicia has a second color different from the first color, wherein a length of each of the second indicia is the same;
    wherein the length of each of the first plurality of indicia is different from the length of each of the second plurality of indicia, and the length of each of the first plurality of indicia and the length of each of the second plurality of indicia is between about 0.5 mm and about 3.0 mm, and
    wherein each of the first plurality of indicia or each of the second plurality of indicia includes a physical attribute extending radially outwards or inwards relative to a longitudinal axis of the at least one expandable leg.

11. The medical device of claim 10, wherein the at least one expandable leg includes the plurality of first indicia and the plurality of second indicia.

12. The medical device of claim 10, wherein the second color of each of the plurality of second indicia is darker than the first color of each of the plurality of first indicia.

13. The medical device of claim 12, wherein the first color of each the plurality of first indicia is white or wherein the first color of each of the plurality of first indicia is blue, and wherein the second color of each of the plurality of second indicia is black.

14. The medical device of claim 10, wherein each of the plurality of first indicia include a first coefficient of friction and each of the plurality of second indicia include a second coefficient of friction, and the second coefficient of friction is greater than the first coefficient of friction.

15. The medical device of claim 10, wherein the end-effector is monolithically formed from a single piece of material.

* * * * *